United States Patent
Johs et al.

(10) Patent No.: US 7,136,172 B1
(45) Date of Patent: Nov. 14, 2006

(54) SYSTEM AND METHOD FOR SETTING AND COMPENSATING ERRORS IN AOI AND POI OF A BEAM OF EM RADIATION

(75) Inventors: Blaine D. Johs, Lincoln, NE (US); Christopher A. Goeden, Lincoln, NE (US); Galen L. Pfeiffer, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 406 days.

(21) Appl. No.: 10/858,795

(22) Filed: Jun. 2, 2004

Related U.S. Application Data (63) Continuation-in-part of application No. 10/652,696, filed on Sep. 2, 2003, and a continuation-in-part of application No. 10/050,802, filed on Jan. 15, 2002, now Pat. No. 6,859,278.

(60) Provisional application No. 60/476,041, filed on Jun. 5, 2003, provisional application No. 60/459,690, filed on Apr. 3, 2003.

(51) Int. Cl.
  *G01B 11/14* (2006.01)
  *G01B 11/24* (2006.01)
(52) U.S. Cl. ..................... 356/614; 356/399
(58) Field of Classification Search ........ 356/364–369, 356/614–623, 399–401; 250/548
See application file for complete search history.

(56) References Cited

U.S. PATENT DOCUMENTS

| | | | | |
|---|---|---|---|---|
| 3,880,524 A | * | 4/1975 | Dill et al. | 356/369 |
| 4,558,949 A | * | 12/1985 | Uehara et al. | 356/139.07 |
| 4,585,348 A | * | 4/1986 | Chastang et al. | 356/369 |
| 4,672,196 A | | 6/1987 | Canino | 250/225 |
| 4,902,900 A | * | 2/1990 | Kamiya et al. | 250/548 |
| 5,166,516 A | * | 11/1992 | Kajimura | 250/234 |
| 5,329,357 A | | 7/1994 | Bernoux et al. | 356/369 |
| 5,373,359 A | | 12/1994 | Woollam et al. | 356/328 |
| 5,517,312 A | | 5/1996 | Finarov | 356/386 |
| 5,596,406 A | | 1/1997 | Rosencwaig et al. | 356/327 |
| 5,801,835 A | * | 9/1998 | Mizutani et al. | 356/614 |
| 5,872,630 A | | 2/1999 | Johs et al. | 356/369 |
| 6,292,259 B1 | * | 9/2001 | Fossey et al. | 356/237.2 |
| 6,969,863 B1 | * | 11/2005 | Foth | 250/559.29 |

FOREIGN PATENT DOCUMENTS

EP    1034413 B1 *    3/2004

* cited by examiner

*Primary Examiner*—Hoa Q. Pham
(74) *Attorney, Agent, or Firm*—James D. Welch (57) ABSTRACT

System and methodology for setting, and compensating detected errors between intended and realized Angle-of-Incidence (AOI) and Plane-Of-Incidence (POI) settings in ellipsometer and the like systems during analysis of sample characterizing data.

18 Claims, 4 Drawing Sheets

SYSTEM AND METHOD FOR SETTING AND COMPENSATING ERRORS IN AOI AND POI OF A BEAM OF EM RADIATION

This Application is a CIP from application Ser. Nos. 10/050,802, Filed Jan. 15, 2002 now U.S. Pat. No. 6,859,278 and 10/652,696, Filed Sep. 2, 2003; and Claims Benefit of Provisional Application 60/476,041 Filed Jun. 5, 2003 and 60/459,690 Filed Apr. 3, 2003.

TECHNICAL FIELD

The disclosed invention relates to systems and method for identifying the angle (AOI) and plane (POI) of incidence of a beam of electromagnetic radiation wit respect to a sample surface, and more particularly to system and methodology for setting an (AOI) and/or (POI) of a beam of electromagnetic radiation to an alignment sample, and/or compensating detected errors between intended and realized Angle-Of-Incidence (AOI) and Plane-Of-Incidence (POI) settings in ellipsometer and the like systems, during analysis of sample characterizing data acquired at actually realized (AOI) and/or (POI) with respect to a sample surface.

BACKGROUND

It is well known that the practice of Reflectometry, Spectrophotometry, Ellipsometry, Polarimetery and the like requires directing electromagnetic beams at samples at known angles (AOI) and planes (POI) of incidence. Typical practice is to set an angle (AOI) and/or plane (POI) of incidence by the directing of an electromagnetic beam and/or the orienting of a sample such that the desired angular relationships are achieved. This can be tedious and requiring of relatively expensive equipment, where high precision is desired. However precise knowledge of the (AOI) and/or (POI) are necessary for achieving accurate analysis of sample characterizing data, and errors between intended and actually achieved (AOI) and/or (POI) lead to errors in analysis.

While present invention systems can be applied in any material system investigation system such as Reflectometer, Spectrophotometer, Polarimeter and the like Systems, an important application is in Ellipsometer Systems, whether Monochromatic or Spectroscopic. It should therefore be understood that Ellipsometry involves acquisition of sample system characterizing data at single or at multiple Wavelengths, and at one or more Angle(s)-of-Incidence (AOI) of a Beam of Electromagnetic Radiation to a surface of the sample system. Ellipsometry is generally well described in a great many number of publications, one such publication being a review paper by Collins, titled "Automatic Rotating Element Ellipsometers: Calibration, Operation and Real-Time Applications", Rev. Sci. Instrum, 61(8) (1990).

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system:

$$\rho = rp/rs = \text{Tan}(\Psi)\exp(i\Delta)$$

Continuing, Ellipsometer Systems generally include a source of a beam of electromagnetic radiation, a Polarizer, which serves to impose a known, (typically linear), state of polarization on a beam of electromagnetic radiation, a Stage for supporting a sample system, and an Analyzer which serves to select a polarization state in a beam of electromagnetic radiation after it has interacted with a sample system, and pass it to a Detector System for analysis therein. As well, one or more Compensator(s) can be present and serve to affect a phase retardance between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). While not limiting, a preferred embodiment is Rotating Compensator (RC) Ellipsometer Systems because they do not demonstrate "Dead-Spots" where obtaining ellipsometric data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have a "Dead Spot" at PSI near 45 Degrees). The utility of Rotating Compensator Ellipsometer Systems should then be apparent. Another benefit provided by Rotating Compensator Ellipsometer Systems is that the Polarizer (P) and Analyzer (A) positions are fixed during data acquisition, and that provides benefit in that polarization state sensitivity to input and output optics during data acquisition is essentially non-existent. This enables relatively easy use of optic fibers, mirrors, lenses etc. for input/output. For insight it is noted that a Patent to Johs, U.S. Pat. No. 5,872,630 describes a material system investigation system comprising a source of a polychromatic beam of electromagnetic radiation, a polarizer, a stage for supporting a sample system, an analyzer, a dispersive optics and at least one detector system which contains a multiplicity of detector elements, said material system investigation system optionally comprising at least one compensator(s) positioned at a location selected from the group consisting of:

before said stage for supporting a sample system, and
after said stage for supporting a sample system, and
both before and after said stage for supporting a sample system;

such that when said material system investigation system is used to investigate a sample system present on said stage for supporting a sample system, at least one of said compensator(s) is/are caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said sample system, pass through said analyzer and interact with said dispersive optics such that a multiplicity of essentially single wavelengths are caused to simultaneously enter a corresponding multiplicity of detector elements in said at least one detector system. Said U.S. Pat. No. 5,872,630 Patent to Johs is also disclosed as it shows use of a Beam Splitter to direct electromagnetic radiation into a Multi-element Alignment Detector (CH).

A Patent to Woollam et al, U.S. Pat. No. 5,582,646 is disclosed as it describes obtaining ellipsometric data through windows in a vacuum chamber, utilizing other than a Brewster Angle of Incidence and analysis of data in sensitive wavelength regions to enhance sensitivity.

Patent to Woollam et al, U.S. Pat. No. 5,373,359 is identified as it shows the presence of a Multi-Element Detector (24) applied to beam alignment in an Ellipsometer System.

Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to Rotating Analyzer ellipsometer systems.

Patent to Bernoux et al., U.S. Pat. No. 5,329,357 is identified as it describes the use of optical fibers as input and output means in an ellipsometer system.

A Patent to Berger et al., U.S. Pat. No. 5,343,293 describes an Ellipsometer which comprises means to direct an electromagnetic beam onto a sample system.

A Patent to Canino, U.S. Pat. No. 4,672,196 describes a system which allows rotating a sample system to control the angle of incidence of a beam of electromagnetic radiation thereonto. Multiple detectors are present to receive the resulting reflected beams.

A Patent to Biork et al., U.S. Pat. No. 4,647,207 describes an ellipsometer system in which reflecting elements are moved into the path of a beam of electromagnetic radiation.

U.S. Pat. No. 5,412,473 to Rosencwaig et al., describes a ellipsometer system which simultaneously provides an electromagnetic beam at a sample surface at numerous angles of incidence thereto.

A European Patent, No. EP 1 034 413 B1 is disclosed as it describes a system for determining an angle of reflection an electromagnetic beam from a sample in an ellipsometer.

Even in view of the prior art, need remains a relatively inexpensive system and methodology which allows easily substantially setting desired (AOI) and/or (POI), wherein said system and method further enable detection of errors between intended and achieved (AOI) and/or (POI), said methodology then providing for correction of said errors during analysis of data acquired at actually realized, as opposed to intended (AOI) and (POI) settings.

DISCLOSURE OF THE INVENTION

The disclosed invention results from the application of various combinations of Alignment and Data Detectors configured to allow use of Alignment Detector output signals to direct physical orienting of samples, and/or to compensate Data Detector output signals for deviations between intended and realized Angle-of-Incidence (AOI) and Plane-of-Incidence (POI) as regards a relationship between a Beam of Electromagnetic Radiation and a Surface of a Sample. As described below, the Alignment Detectors can comprise a central hole through which the Beam of Electromagnetic Radiation passes, enroute to interaction with a Sample, or after an interaction therewith, or can receive a portion of a Beam of Electromagnetic Radiation directed thereto by a Beam Splitter. The Beam can be directed into a Data Detector directly, or can be focused onto an end of an optical fiber which conveys Electromagnetic Radiation to a Data Detector.

In use, the disclosed invention applies signals from Multi-Element Alignment Detectors, (eg. Quad Detectors), in detection of actually achieved, as opposed to intended, Angle-of-Incidence (AOI) and Plane-of-Incidence (POI) alignment of beams of electromagnetic radiation, with respect to a Sample Surface. While signals developed by the Multi-Element Alignment Detectors in precision systems can be used to enable physical adjustment of the location and/or orientation of samples, and/or that of a source and detector of a beam electromagnetic radiation, which beam is caused to interact with a sample, the disclosed invention teaches utilization of signals from Multi-element Alignment Detectors which monitor incident and/or reflected beams of electromagnetic radiation, to provide information about errors between intended and actually achieved (AOI) and/or (POI). Said information can then be utilized to enable compensation of identified errors between intended and realized (AOI) and/or (POI) during analysis of data provided by a Data Detector. While not abandoning the practice of physical Sample orientation adjustment, the present invention teaches applying data which identifies actually achieved and known (AOI) and/or (POI) values to compensate Sample characterizing data, and therefore does not require expensive systems which are capable of precisely physically setting intended (AOI) and/or (POI) to intended values.

One version of the disclosed invention provides for use of multiple element alignment detectors in the monitoring of an electromagnetic beam reflected from a sample which is then focused to enter an accessible end of an optical fiber, as opposed to directing said reflected electromagnetic beam directly into a data detector.

Further, some embodiments systems of the disclosed invention utilize beam splitters to provide a portion of an electromagnetic beam to the multi-element alignment detector, with the remainder of the electromagnetic beam being directed toward and detected by at least one data detector, again, possibly via an optical fiber. In other embodiments a multi-element detector provides a hole through which a beam of electromagnetic radiation passes in use.

It is also noted that where a sample is aligned so that exactly the intended (AOI) and (POI) are achieved, rotating of the sample about an axis perpendicular to the surface thereof, (eg. Generalized Ellipsometry), as might be done to investigate anisotropy in a sample can result in achieving other than the intended (AOI) and/or (POI) at various rotation positions. Readjustment of the (AOI)/(POI) at each rotation setting is typically not practical, but the disclosed invention correction procedure to compensate the (AOI) and/or (POI) at various rotation settings during data analysis can be relatively easily implemented. In light of the foregoing it is noted that where a complete 360 degree rotation of a sample about the axis perpendicular to the surface thereof can provide data which is zone averaged to aid with compensating differences in (POI) at different rotation settings, such an approach to compensating (AOI), which can vary at each rotation setting, is not applicable.

A disclosed invention method of characterizing a sample utilizing a beam of electromagnetic radiation then comprises the steps of:

a) providing an alignment sample and a source of electromagnetic radiation and a data detector;

b) orienting the alignment sample such that a beam of electromagnetic radiation produced by said source is caused to obliquely impinge thereupon, reflect therefrom and enter the data detector at a base angle-of-incidence and plane-of-incidence;

c) causing a portion of the beam of electromagnetic radiation reflected from the sample to enter a multi-element alignment detector, and positioning said multi-element alignment detector so that signals can be developed by each of its elements;

d) removing said alignment sample and placing a test sample in its place;

e) obtaining data from said test sample by causing electromagnetic radiation from said source to reflect from said test sample and enter said data detector;

f) to characterize said test sample, analyzing the data obtained from the detector in step e in combination with signals from the elements of the multi-element alignment detector which identifies differences from signals determined in step c, said difference signals serving to provide information sufficient to compensate differences in intended and actually realized angle-of-incidence and plane-of-incidence of the test sample as compared to the base angle-of-incidence and plane-of-incidence of the alignment sample in step b.

Said method can further comprise the steps of:

a') providing a second source of a beam of electromagnetic radiation positioned above said sample, and a second multiple element alignment detector which provides a substantially centrally located hole therein, each element of said second multiple element alignment detector being positioned to receive substantially equal amounts of a beam of electromagnetic radiation provided by said second source thereof after passing through said substantially centrally located hole and reflecting from said sample when it is oriented perpendicular to said beam of electromagnetic radiation;

b') causing said second source of electromagnetic radiation to provide a beam of electromagnetic radiation which is directed toward said substantially centrally located hole; and c') monitoring reflected electromagnetic radiation from said sample which enters each element of said multiple element alignment detector and adjusting the orientation of said sample until said multiple elements detect approximately amounts of electromagnetic radiation, and/or utilizing said signals developed by the elements of the multi-element detector to compensate differences in intended and actually realized angle-of-incidence and plane-of-incidence of the test sample as compared to the base angle-of-incidence and plane-of-incidence of the alignment sample in step b.

A modified application of the disclosed invention method enables the maintaining of the spatial relationship between the focal point of a lens and the end of a optical fiber which directs electromagnetic radiation into a data detector in an ellipsometer or the like system, and comprises the steps of:

a) providing an alignment sample and a source of electromagnetic radiation and a optical fiber with an accessible end;

practicing steps b and c simultaneously:

b) orienting the alignment sample such that a beam of electromagnetic radiation produced by said source is caused to obliquely impinge thereupon, reflect therefrom, and via the focusing lens enter the accessible end of said optical fiber;

c) causing a portion of the beam of electromagnetic radiation reflected from the sample to enter a multi-element alignment detector via a focusing lens, and positioning said multi-element alignment detector so that signals are developed by each of its elements;

d) removing said alignment sample and placing a test sample in its place;

e) adjusting the orientation of the test sample so that the multi-element alignment detector provides substantially the same output signals as was developed in step c is achieved; with the result being that the portion of the electromagnetic beam not caused to enter said multi-element alignment detector via a focusing lens, is caused to enter the accessible end of the optical fiber.

Said method can further comprise:

providing a data detector attached to a distal end of said optical fiber so that electromagnetic radiation entered to said optical fiber is detected by said data detector; and characterizing said test sample by analyzing the data obtained from the data detector in combination with signals from the elements of the multi-element alignment detector.

Practice of this method will typically require use of output signals from the multi-element alignment detector to physically re-orient the test sample, however, where the beam is focused other than perfectly onto the end of the optical fiber, but sufficiently well focused thereupon to convey input to the data detector, the multi-element alignment detector signals can be utilized as described before to mediate compensation of data detector output for actually achieved, as opposed to intended, AOI and POI settings.

It is noted that an uneven intensity of the beam of electromagnetic radiation produced by said source, (eg. caused by a partial blocking thereof), over its cross-section can also cause a change in the output of the multiple element detector which can be at least partially compensated by practice of the recited method.

In the foregoing recited methods, typically the portion of the beam of electromagnetic radiation reflected from the sample and caused to enter the multi-element detector in step c is produced by a beam splitter, and the signals developed by each of the elements of the multi-element detector in step c are caused to be equal at desired angle-of-incidence (AOI) and plane-of-incidence (POI) conditions.

Another presently disclosed method of characterizing a sample utilizing a beam of electromagnetic radiation, comprises the steps of:

a) providing an alignment sample, a source electromagnetic radiation and a data detector;

b) orienting the alignment sample such that a beam of electromagnetic radiation produced by said source is caused to obliquely impinge thereupon, reflect therefrom and enter the data detector at a base angle-of-incidence and plane-of-incidence;

c) causing a portion of the beam of electromagnetic radiation reflected from the sample to enter a multi-element alignment detector, and positioning said multi-element alignment detector so that known signals can be developed by each of its elements;

d) while changing the orientation of said alignment sample through a multiplicity of known angle-of-incidence and plane-of-incidence combinations, obtaining a data set which corresponds to signals from each from said multi-element detector element;

e) removing said alignment sample and placing a test sample in its place and orienting it generally as was the alignment sample in step b;

f) obtaining data from said test sample by causing electromagnetic radiation from said source to reflect from said test sample and enter said data detector;

g) characterizing said test sample by analyzing the data obtained from the detector in step f, in combination with correction parameters based on signals from the elements of the multi-element alignment detector which identify what angle-of-incidence and plane-of-incidence combination actually characterizes the test sample orientation, said correction parameters being based on data determined in step d.

Said method can involve a portion of the beam of electromagnetic radiation reflected from the sample being caused to enter the multi-element alignment detector in step c via beam splitter.

Said method can involve using signals developed by each of the elements said multi-element alignment detector to physically effect desired AOI and POI orientation of the sample.

Said method can further comprise the steps of:

a') providing a second source of a beam of electromagnetic radiation positioned above said sample, and a second multiple element alignment detector, each element of said second multiple element alignment detector being positioned to receive substantially equal amounts of a beam of electromagnetic radiation provided by said second source thereof after reflecting from said alignment sample when it is oriented perpendicular to said beam of electromagnetic radiation;

b') causing said second source of electromagnetic radiation to provide a beam of electromagnetic radiation which is directed toward said alignment sample; and c') while changing the orientation of said alignment sample through a multiplicity of known angle-of-incidence and plane-of-incidence combinations, obtaining a data set which corresponds to signals from each from said multi-element alignment detectors;

d') utilizing said data set to provide a further correction factor to apply to data in step g for the angle-of-incidence and plane-of-incidence combination which actually characterizes the test sample orientation.

It is noted that the alignment detector associated with said second source of electromagnetism can have a centrally oriented hole therein through which said beam of electromagnetic radiation from said second source passes before impinging on said alignment sample, or said alignment detector can receive electromagentic radiation from a beam splitted which directs a part of the beam of electromagnetic radiation from said second source thereinto which the remainder thereof passes impinges on said alignment sample.

Another presently disclosed method of characterizing a sample utilizing a beam of electromagnetic radiation, comprising the steps of:

a) providing an alignment sample and a first source of electromagnetic radiation and a data detector;

b) orienting the alignment sample such that a beam of electromagnetic radiation produced by said first source is caused to obliquely impinge thereupon, reflect therefrom and enter the data detector;

c) providing a second source of a beam of electromagnetic radiation positioned above said sample, and a multiple element alignment detector which provides a substantially centrally located hole therein, each element of said second multiple element alignment detector being positioned to receive substantially equal amounts of a beam of electromagnetic radiation provided by said second source thereof after passing through said substantially centrally located hole and reflecting from said alignment sample when it is oriented perpendicular to said beam of electromagnetic radiation from said second source;

d) causing said second source of electromagnetic radiation to provide a beam of electromagnetic radiation which is directed toward said substantially centrally located hole;

e) while changing the orientation of said alignment sample through a multiplicity of known angle-of-incidence and plane-of-incidence combinations, obtaining a data set which corresponds to signals from each of said multi-element alignment detectors;

f) removing said alignment sample and placing a test sample in its place and orienting it generally as was the alignment sample in step b;

g) obtaining data from said test sample by causing electromagnetic radiation from said first source to reflect from said test sample and enter said data detector;

h) characterizing said test sample by analyzing the data obtained from the detector in step g, in combination with correction parameters based on signals from the elements of the multi-element alignment detectors which identify what angle-of-incidence and plane-of-incidence combination characterizes the actual test sample orientation, said correction parameters being based on the data set determined in step e.

Note, the "data sets" provided by output from a multi-element alignment detector just identified can comprise signal intensities from each element thereof in identified correspondence with alignment sample angle-of-incidence and plane-of-incidence combinations. An example Data Set might appear as:

| FOR A FIRST SET AOI AND POI | |
|---|---|
| OUTPUT FROM ALIGNMENT DETECTOR ELEMENTS | CORRESPONDING ACTUAL AOI & POI |
| ELEMENT 1 INTENSITY ELEMENT 2 INTENSITY ELEMENT 3 INTENSITY ELEMENT 4 INTENSITY . . . ELEMENT N INTENSITY | AOI = YYY.YY DEGREES POI = XXX.XX DEGREES |

| FOR A SECOND SET AOI AND POI | |
|---|---|
| OUTPUT FROM ALIGNMENT DETECTOR ELEMENTS | CORRESPONDING ACTUAL AOI & POI |
| ELEMENT 1 INTENSITY ELEMENT 2 INTENSITY ELEMENT 3 INTENSITY ELEMENT 4 INTENSITY . . . ELEMENT N INTENSITY ETC. | AOI = YYY.YY DEGREES POI = XXX.XX DEGREES | said data set having a multiplicity of additional similar known angle-of-incidence and plane-of-incidence setting combinations as set in Step e in the just preceding example, and corresponding actual AOI and POI values.

It is also mentioned that use of the terminology "above" is not meant to limit the invention to the case wherein a second source of a beam of electromagnetic radiation positioned above said sample is "above" only in the sense of laboratory coordinates. That is, rotating the ellipsometer or the like system so that the second source is not above the sample in laboratory coordinates does not remove the system from the Claims as said terminology is used herein.

It is also noted that the disclosed invention system can operate at at least one wavelength in at least one wavelength range, such as:

RADIO;
MICROWAVE;
FIR;
IR;
NIR-VIS-NUV;
UV;
DUV;
VUV;
EUV;
XRAY.

The described invention can be practiced in any type of reflectometer or ellipsometer, (eg. Rotating Polarizer, Rotating Analyzer, Rotating Compensator, Modulation Element).

The disclosed invention will be better understood by reference to the Detailed description Section, in conjunction with the Drawings.

SUMMARY OF THE INVENTION

A primary purpose and/or objective of the disclosed invention is to teach a system for enabling detection and correction of errors in AOI and/or POI in analysis of sample characterizing data produced by material system investigation systems such as ellipsometers, polarimeters, reflectometers, spectrophotometers and the like systems.

Another primary purpose and/or objective of the disclosed invention is to teach a system for maintaining the spatial relationship between, for instance, the focal point of a lens and the end of an optical fiber which directs electromagnetic radiation to a detector in an ellipsometer or the like system.

It is another purpose and/or objective of the disclosed invention is to teach construction of a Data Set by, while changing the orientation of said alignment sample through a multiplicity of known angle-of-incidence (AOI) and plane-of-incidence (POI) combinations, obtaining a data set which corresponds to signals from each from said multi-element alignment detector. Said "Tabulated" Data Set which identifies combinations of Alignment Detector Elements outputs to an AOI and POI combination can be applied to compensate AOI and/or POI values during analysis of Sample Characterizing Data obtained from a Data Detector.

Other purposes and/or objectives will become obvious from a reading of the Specification and Claims.

DETAILED DESCRIPTION

Figure 1A:
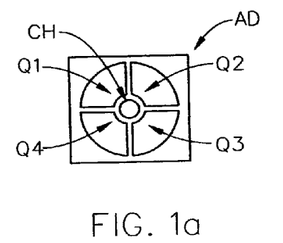
FIGS. 1a and 1b show multiple-element detectors (AD).
Figure 1B:
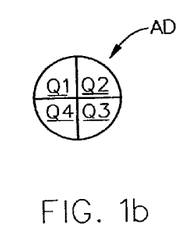

FIGS. 1a and 1b show multiple-element detectors (AD). FIG. 1a shows a Quad-Detector with four detector regions (Q1), (Q2), (Q3) and (Q4). Note also the presence of a central hole (CH). FIG. 1b shows a Quad-detector (AD) with four detector regions (Q1), (Q2), (Q3) and (Q4) which are more closely packed and no central hole is present.

Figure 2:
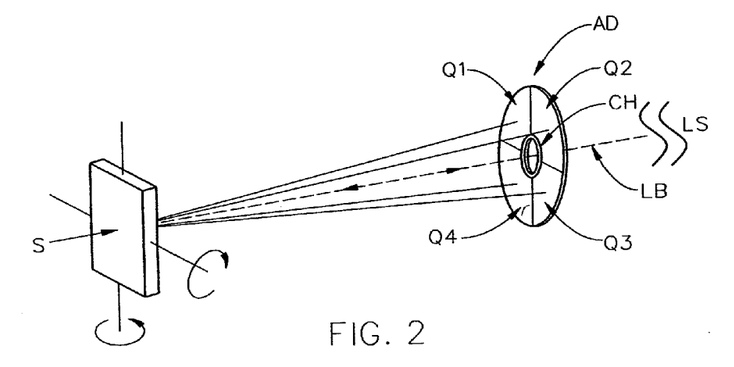
FIGS. 2 and 3 demonstrate an approach to setting an angle-of-incidence using a FIG. 1a type multiple element detector.
Figure 3:
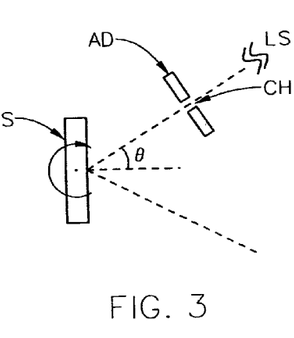

FIGS. 2 and 3 demonstrate an approach to setting an angle-of-incidence using a FIG. 1a type multiple element detector. Said approach involves providing a beam of electromagnetic radiation (LB) from Source (LS), which beam (LB) is caused to pass through central hole (CH) in multiple element detector (AD) and reflect from Sample (S). Sample (S) is rotated so that equal amounts of electromagnetic radiation reflect to the four detector regions (Q1), (Q2), (Q3) and (Q4). Once the beam (LB) is thus caused to be oriented perpendicular to the surface of the Sample (S) it is rotated through a known angle (θ) as shown in FIG. 3, thereby providing a known angle of incidence of (θ) to the Sample (S).

Figure 4:
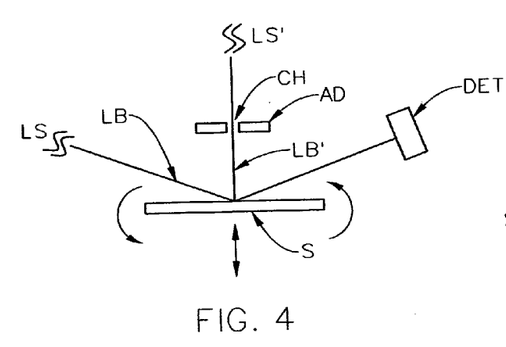
FIG. 4 demonstrates a multiple element detector positioned vertically above a sample (S).

FIG. 4 demonstrates a FIG. 1a type multiple element detector (AD) positioned vertically above a sample (S). In use the Sample a beam (LB') of electromagnetic radiation is provided by Source (LS') and Sample (S) is rotated around orthogonal axes so that the various detector elements in the FIG. 1a type multiple element detector (AD) receive substantially equal amounts of reflected radiation, thereby showing that the surface of the Sample, at the point the beam (LB') is oriented perpendicular to said beam (LB'). This approach has the benefit that vertical motion of the Sample (S) has no effect on the alignment process of the Sample (S).

Figures 5, 6:
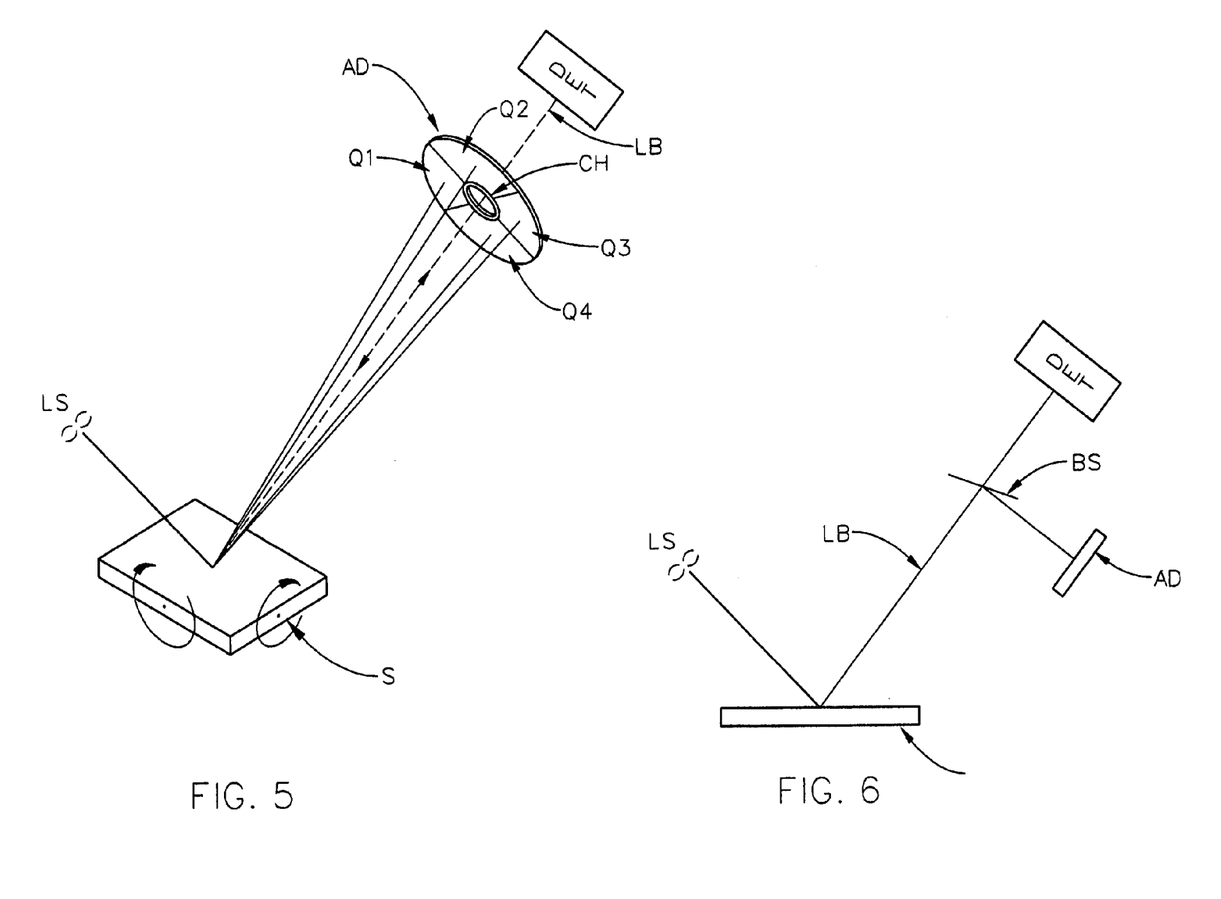
FIG. 5 shows use of a multiple element detector (AD) through which a reflected electromagnetic beam (LB) passes before entering a detector (DET).
FIG. 6 shows a beam splitter (BS) in a reflected electromagnetic beam (LB) passes before entering a detector (DET), which beam splitter directs a portion of the electromagnetic beam into a FIG. 1b type multiple element detector.

FIG. 5 shows use of a multiple element detector (AD) through which a reflected electromagnetic beam (LB) passes before entering a detector (DET). When Sample (S) is properly aligned so that beam (LB) proceeds to Detector (DET) as desired, the detector elements (Q1), (Q2), (Q3) and (Q4) each provide substantially the same output.

FIG. 6 shows a beam splitter (BS) in a reflected electromagnetic beam (LB) passes before entering a detector (DET), which beam splitter directs a portion of the electromagnetic beam into a FIG. 1b type multiple element detector. Again, when Sample (S) is properly aligned so that a portion of beam (LB) proceeds to Detector (DET) as desired, the detector elements (Q1), (Q2), (Q3) and (Q4) each provide substantially the same output.

Figure 7:
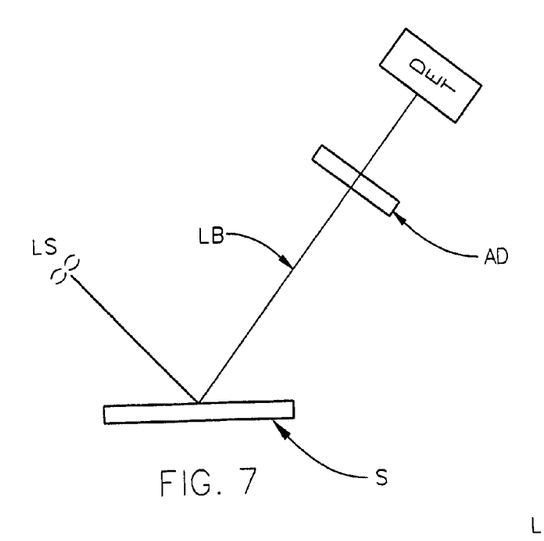
FIG. 7 shows a multiple element detector (AD) in a reflected electromagnetic beam (LB) passes before entering a detector (DET).

FIG. 7 shows a multiple element detector (AD) in a reflected electromagnetic beam (LB) passes before entering a detector (DET). FIG. 7 is basically a side view of the situation shown in perspective in FIG. 5.

Figure 8:
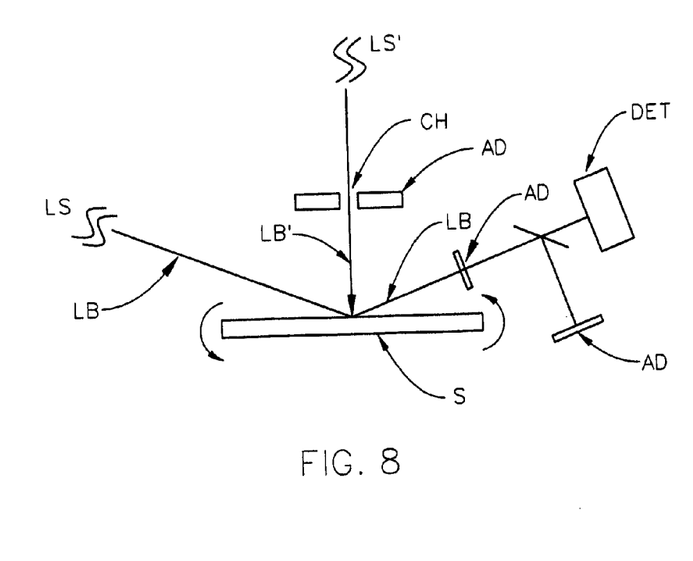
FIG. 8 shows a combined system comprising three multiple element detectors shown separately in FIGS. 4, 6 and 7.

FIG. 8 shows a combined system comprising three multiple element detectors each identified as (AD), and which are shown separately in FIGS. 4, 6 and 7. With all such multiple element detectors (AD) are available output from each can be utilized or not as is found to be optimum.

Figure 9:
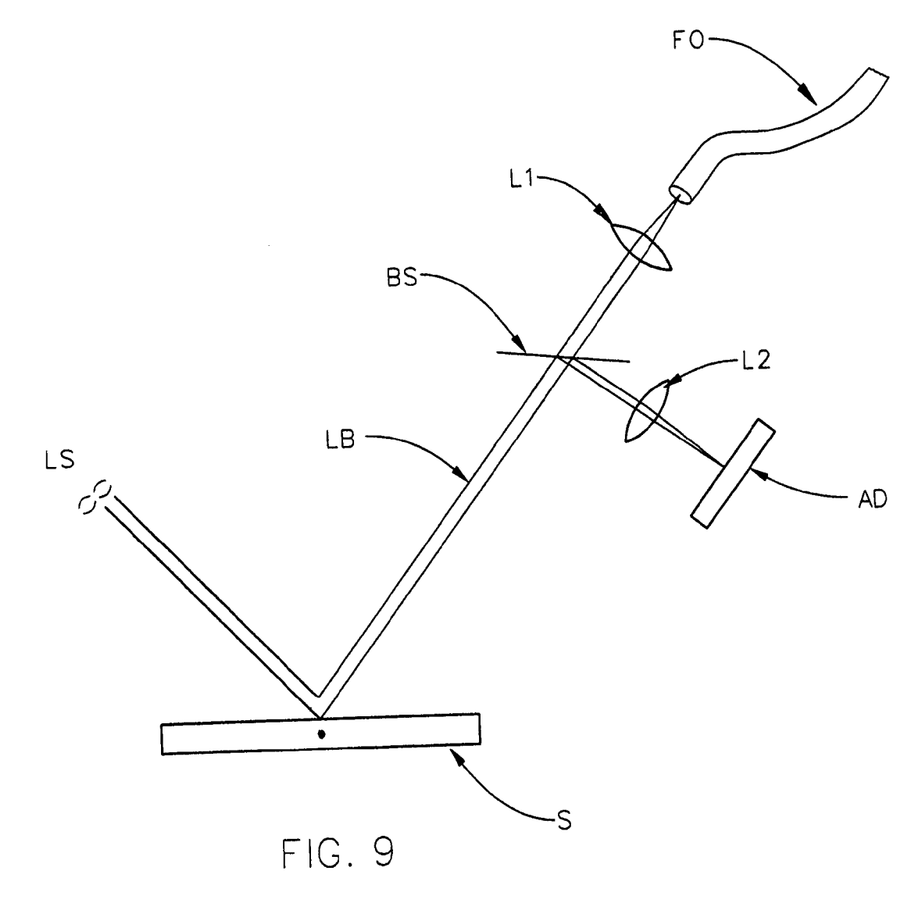
FIG. 9 demonstrates use of a multiple element detector (AD) which, via a beam splitter (BS), receives a focused portion of an electromagnetic beam (LB) reflected from a sample (S), the remainder of said electromagnetic beam (LB) is focused into an accessible end of a fiber optic (FO).

FIG. 9 demonstrates use of a multiple element detector (AD) which, via a beam splitter (BS), receives a focused portion of an electromagnetic beam (LB) reflected from a sample (S), the remainder of said electromagnetic beam (LB) is focused into an accessible end of a fiber optic (FO). After calibration to properly coordinated equal output from each of the alignment detector elements (Q1), (Q2), (Q3) and (Q4) to proper placement of focus point by Lens (L1), it should be appreciated that monitoring output of the alignment detector elements (Q1), (Q2), (Q3) and (Q4) and response to change therein can be used to keep the beam focused by Lens (L1) properly positioned on the accessible end of the Fiber Optic (FO). Further, after the initial orienting of a sample via physical motion, signals developed by alignment detector elements (Q1), (Q2), (Q3) and (Q4) can be applied to compensate minor deviations of AOI and POI from intended values. Note also that a Lens (L2) is present to focus the portion of the beam (LB) which is directed threat by Beam Splitter (BS). It is noted that a similar arrangement could be substituted for the Alignment Detectors (AD) shown in FIGS. 4 and 8.

It is also possible to use a signal generated by a multiple element detector (AD) to adjust the vertical height of a Sample (S), as the system in FIG. 4 can be alternatively interpreted to show by realizing that if the sample height is not appropriate to direct the reflected beam onto the multiple element alignment detector elements (Q1), (Q2), (Q3) and (Q4), no signal will be developed thereby.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of characterizing a sample utilizing a beam of electromagnetic radiation, comprising the steps of:
   a) providing an alignment sample, a source of electromagnetic radiation and data detector;
   b) orienting the alignment sample such that a beam of electromagnetic radiation produced by said source is caused to obliquely impinge thereupon, reflect therefrom and enter the data detector at a base angle-of-incidence and plane-of-incidence;
   c) causing a portion of the beam of electromagnetic radiation reflected from the alignment sample to enter a multi-element alignment detector, and positioning said multi-element alignment detector so that signals are developed by each of its elements;
   d) removing said alignment sample and placing a test sample in its place;
   e) obtaining data from said test sample by causing electromagnetic radiation from said source to reflect from said test sample and enter said data detector;
   f) characterizing said test sample by analyzing the data obtained from the data detector in step e, in combination with signals from the elements of the multi-element alignment detector which identify differences from signals determined in step c, said difference signals serving to provide information to compensate offsets in intended and actually realized angle-of-incidence and plane-of-incidence of the test sample as compared to the base angle-of-incidence and plane-of-incidence of the alignment sample in step b.

2. A method as in claim 1 in which the signals developed by each of the elements of the multi-element alignment detector in step c are caused to be equal.

3. A method as in claim 1 in which the portion of the beam of electromagnetic radiation reflected from the sample and caused to enter the multi-element alignment detector in step c is produced by a beam splitter.

4. A method as in claim 1 in which the signals developed by each of the elements said multi-element detector are utilized to effect angle-of incidence and/or plane-of-incidence test sample orientation.

5. A method as in claim 1 in which further comprises the steps of:
   a') providing a second source of a beam of electromagnetic radiation positioned above said alignment sample, and a second multiple element alignment detector which provides a substantially centrally located hole therein, each element of said second multiple element alignment detector being positioned to receive substantially equal amounts of a beam of electromagnetic radiation provided by said second source thereof after passing through said substantially centrally located hole and reflecting from said alignment sample when it is oriented perpendicular to said beam of electromagnetic radiation;
   b') causing said second source of electromagnetic radiation to provide a beam of electromagnetic radiation which is directed toward said substantially centrally located hole; and
   c') monitoring reflected electromagnetic radiation from said alignment sample which enters each element of said multiple element alignment detector and performing a selection from the group consisting of:
      adjusting the orientation of said sample until said multiple elements detect approximately equal amounts of electromagnetic radiation; and
      utilizing said data to compensate offsets in intended and actually realized angle-of incidence and plane-of-incidence of the test sample as compared to the base angle-of-incidence and plane-of-incidence of the alignment sample in step b.

6. A method of maintaining the spatial relationship between the focal point of a lens and the end of a optical fiber which directs electromagnetic radiation to a detector in an ellipsometer or the like system, comprising the steps of:
   a) providing an alignment sample and a source of electromagnetic radiation and a optical fiber with an accessible end;
   b) orienting the alignment sample such that a beam of electromagnetic radiation produced by said source is caused to obliquely impinge thereupon, reflect therefrom, and via a focusing lens enter the accessible end of said optical fiber;
   c) causing a portion of the beam of electromagnetic radiation reflected from the sample to enter a multi-element alignment detector via a focusing lens, and positioning said multi-element alignment detector so that signals are developed by each of its elements;
   d) removing said alignment sample and placing a test sample in its place;
   e) adjusting the orientation of the test sample so that the multi-element alignment detector provides substantially the same output as was developed in step c is achieved;

with the result being that the portion of the electromagnetic beam not caused to enter said multi-element alignment detector, is caused to enter the accessible end of the optical fiber via said focusing lens.

7. A method as in claim 6 in which the portion of the beam of electromagnetic radiation reflected from the sample and caused to enter the multi-element alignment detector in step c is produced by a beam splitter.

8. A method as in claim 6 which further comprises:
providing a data detector attached to a distal end of said optical fiber so that electromagnetic radiation entered to said optical fiber is detected by said data detector; and
characterizing said test sample by analyzing the data obtained from the data detector in combination with signals from the elements of the multi-element alignment detector.

9. A method as in claim 6 in which the known signals developed by each of the elements said multi-element detector are utilized to effect vertical position of the sample.

10. A method of characterizing a sample utilizing a beam of electromagnetic radiation, comprising the steps of:
a) providing an alignment sample, a source of electromagnetic radiation and data detector;
b) orienting the alignment sample such that a beam of electromagnetic radiation produced by said source is caused to obliquely impinge thereupon, reflect therefrom and enter the data detector at a base angle-of-incidence and plane-of-incidence;
c) causing a portion of the beam of electromagnetic radiation reflected from the sample to enter a multi-element alignment detector, and positioning said multi-element alignment detector so that signals are developed by each of its elements;
d) while changing the orientation of said alignment sample through a multiplicity of known angle-of-incidence and plane-of-incidence combinations, obtaining a data set which corresponds to signals from each from said multi-element detector;
e) removing said alignment sample and placing a test sample in its place and orienting it generally as was the alignment sample in step b;
f) obtaining data from said test sample by causing electromagnetic radiation from said source to reflect from said test sample and enter said data detector;
g) characterizing said test sample by analyzing the data obtained from the data detector in step f, in combination with correction parameters based on signals from the elements of the multi-element detector which identify what angle-of-incidence and plane-of-incidence combination actually characterizes the test sample orientation, said correction parameters being based on data in the data set determined in step d.

11. A method as in step 10 which involves a portion of the beam of electromagnetic radiation reflected from the sample being caused to enter the multi-element alignment detector in step c via beam splitter.

12. A method as in step 10 which involves using signals developed by each of the elements of said multi-element alignment detector to effect the orientation of the sample.

13. A method as in step 10 which further comprises the steps of:
a') providing a second source of a beam of electromagnetic radiation positioned above said sample, and a second multiple element alignment detector, each element of said second multiple element alignment detector being positioned to receive substantially equal amounts of a beam of electromagnetic radiation provided by said second source thereof after reflecting from said alignment sample when it is oriented perpendicular to said beam of electromagnetic radiation;
b') causing said second source of electromagnetic radiation to provide a beam of electromagnetic radiation which is directed toward said alignment sample; and
c') while changing the orientation of said alignment sample through a multiplicity of known angle-of-incidence and plane-of-incidence combinations, obtaining a data set which corresponds to signals from each from said multi-element alignment detectors;
d') utilizing said data set to provide a further correction factor to apply to data in step g for the angle-of-incidence and plane-of-incidence combination which actually characterizes the test sample orientation.

14. A method as in step 13, in which the alignment detector has a centrally oriented hole therein through which said beam of electromagnetic radiation from said second source passes before impinging on said alignment sample.

15. A method as in step 13, in which the alignment detector receives electromagentic radiation from a beam splitted which directs a part of the beam of electromagnetic radiation from said second source thereinto which the remainder thereof passes impinges on said alignment sample.

16. A method of characterizing a sample utilizing a beam of electromagnetic radiation, comprising the steps of:
a) providing an alignment sample and a first source of electromagnetic radiation and a data detector;
b) orienting the alignment sample such that a beam of electromagnetic radiation produced by said first source is caused to obliquely impinge thereupon, reflect therefrom and enter said data detector;
c) providing a second source of a beam of electromagnetic radiation positioned above said sample, and a multiple element alignment detector which provides a substantially centrally located hole therein, each element of said second multiple element alignment detector being positioned to receive substantially equal amounts of a beam of electromagnetic radiation provided by said second source thereof after passing through said substantially centrally located hole and reflecting from said alignment sample when it is oriented perpendicular to said beam of electromagnetic radiation;
d) causing said second source of electromagnetic radiation to provide a beam of electromagnetic radiation which is directed toward said substantially centrally located hole;
e) while changing the orientation of said alignment sample through a multiplicity of known angle-of-incidence and plane-of-incidence combinations, obtaining a data set which corresponds to signals from each of the elements of said multi-element alignment detector;
f) removing said alignment sample and placing a test sample in its place and orienting it generally as was the alignment sample in step b;
g) obtaining data from said test sample by causing electromagnetic radiation from said first source to reflect from said test sample and enter said data detector;
h) characterizing said test sample by analyzing the data obtained from the detector in step g, in combination with correction parameters based on signals from the elements of the multi-element alignment detectors which identify what angle-of-incidence and plane-of-incidence combination actually characterizes the test sample orientation, said correction parameters being based on the data set determined in step e.

17. A method as in claim 16 which further comprises providing a beam splitter such that a portion of the beam of electromagnetic radiation produced by said first source which is caused to obliquely impinge upon, reflect from and enter said data detector is diverted into a second multiple element alignment detector and further, after step b, monitoring electromagnetic radiation from said first source thereof which reflects from said alignment sample and enters each element of said second multiple element alignment detector and adjusting the vertical height and/or orientation of said alignment sample until said multiple elements detect approximately equal amounts of electromagnetic radiation.

18. A method as in claim 16 which further comprises providing a beam splitter such that a portion of the beam of electromagnetic radiation produced by said first source, which is caused to obliquely impinge upon said sample, reflect therefrom and enter said data detector is diverted into a second multiple element alignment detector and further, in step h, utilizing signals developed by the elements of said second multiple element alignment detector to compensate offsets in intended and actually realized angle-of incidence and plane-of-incidence of the test sample.

* * * * *